US012751617B2

(12) United States Patent
Padula

(10) Patent No.: US 12,751,617 B2
(45) Date of Patent: Oct. 6, 2026

(54) LYME RELATED INFECTION INDICATOR

(71) Applicant: DR RP HOLDINGS, LLC, Louisville, KY (US)

(72) Inventor: William Padula, Guilford, CT (US)

(73) Assignee: DR RP HOLDINGS, LLC, Louisville, KY (US)

( * ) Notice: Subject to any disclaimer, the term of this patent is extended or adjusted under 35 U.S.C. 154(b) by 658 days.

(21) Appl. No.: 18/312,939

(22) Filed: May 5, 2023

(65) Prior Publication Data

US 2023/0355091 A1 Nov. 9, 2023

Related U.S. Application Data

(60) Provisional application No. 63/338,954, filed on May 6, 2022.

(51) Int. Cl.
*A61B 3/12* (2006.01)
*A61B 3/10* (2006.01)
*G06T 7/11* (2017.01)

(52) U.S. Cl.
CPC ............ *A61B 3/1233* (2013.01); *A61B 3/102* (2013.01); *G06T 7/11* (2017.01); *G06T 2207/10101* (2013.01); *G06T 2207/30041* (2013.01); *G06T 2207/30104* (2013.01)

(58) Field of Classification Search
None
See application file for complete search history.

(56) References Cited

PUBLICATIONS

Padula and Sayyed, International Journal of Infectious Diseases, 2023, 133:5-8 (Year: 2023).*

Randy Schulman, Natural Awakenings, Eye on Lyme Disease: Visual Symptoms and Effects Often Overlooked, Apr. 1, 2017, accessed on Nov. 18, 2025 from www.enaturalawakenings.com/2017/04/01/234440/eye-on-lyme-disease-visual-symptoms-and-effects-often-overlooked, 7 pages (Year: 2017).*

Murray T and Shapiro E, "Lyme Disease", Clin Lab Med, Mar. 2010, vol. 30(1), pp. 311-328.

Ostrov B and Athreya B, "Lyme Disease: Difficulties in Diagnosis and Management", Pediatric Clinics of North America, Jun. 1991, vol. 38, No. 3, pp. 535-553.

Ghassemi F et al., "The Quantitative Measurement of Vascular Density and Flow Areas of Macula Using Optical Coherence Tomography Angiography in Normal Volunteers", Ophthalmic Surg Lasers Imaging Retina, 2017, 48(6), pp. 478-486.

Saito H et al., "Optic Disc and Peripapillary Morphology in Unilateral Nonarteritic Anterior Ischemic Optic Neuropathy and Age- and Refraction-Matched Normals", Othalmology, Sep. 2008, 115(9), pp. 1585-1590.

Pemp B et al., "Calculation of central retinal artery diameters from non-invasive ocular haemodynamic measurements in type 1 diabetes patients", Acta Ophthalmol., 2013, 91, e348-e352.

Knoop F, "Borrelia Infections", Elsevier, 2014, Reference Module in Biomedical Sciences, 3 pages.

Campbell J et al., "Detailed Vascular Anatomy of the Human Retina by Projection-Resolved Optical Coherence Tomography Angiography", Scientific Reports, 2017, (7)42201, 11 pages.

Sapi E et al., "Characterization of Biofilm Formation by Borrelia burgdorferi In Vitro", PLoS One, 2012, vol. 7(10). 11 pages.

Miller N and Arnold A, "Current concepts in the diagnosis, pathogenesis and management of nonarteritic anterior ischaemic optic neuropathy", Eye, 2015, vol. 29(1), pp. 65-79.

Rader J et al., "Peripapillary Vasoconstriction in the Glaucomas and the Anterior Ischemic Optic Neuropathies", American Journal of Ophthalmology, Jan. 1994, vol. 117(1), pp. 72-80.

Park J et al., "Peripapillary Vessel Density in Young Patients with Open-Angle Glaucoma: Comparison between High-Tension and Normal-Tension Glaucoma", Scientific Reports, 2019, 10 pages.

Caprioli, J and Spaeth G, "Comparison of the Optic Nerve Head in High- and Low-Tension Glaucoma", Arch Ophthalmol., Aug. 1986, vol. 103, pp. 1145-1149.

* cited by examiner

*Primary Examiner* — Stacy B Chen
(74) *Attorney, Agent, or Firm* — GrayRobinson, P.A.

(57) ABSTRACT

Methods for identifying indications for testing for Lyme related infection are described. A subject, presenting a sudden onset of at least one visual symptom known to be associated with Lyme related infection, may be screened for peri-papillary ischemia and, if peri-papillary ischemia is present, the subject may be recommended to undergo further testing for Lyme related infection.

17 Claims, 6 Drawing Sheets

Figure 2A
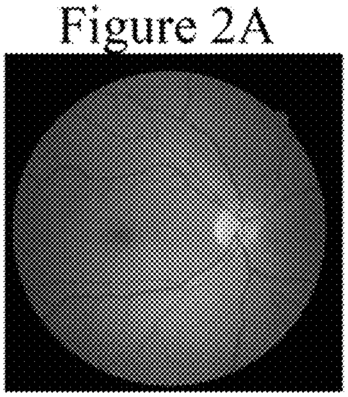
Figure 2B
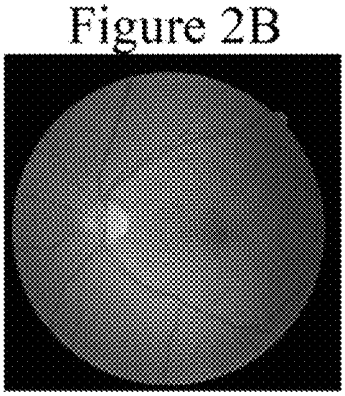
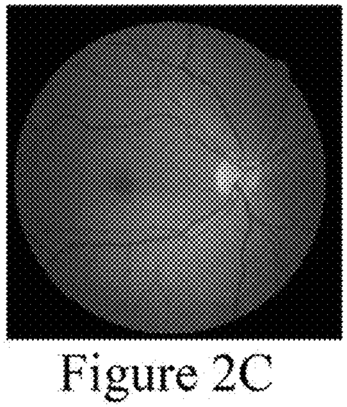
Figure 2C
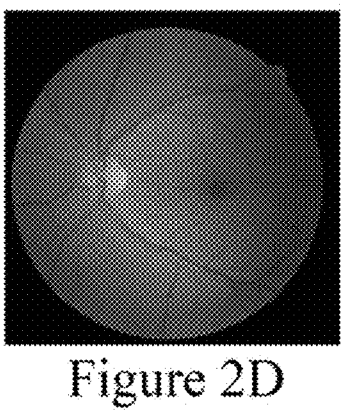
Figure 2D

Vessel Density (RPC)

Vessel Density (RPC)

Vessel Density (RPC)

Vessel Density (RPC)

LYME RELATED INFECTION INDICATOR

CROSS-REFERENCE TO RELATED APPLICATION

This application claims priority under 35 U.S.C. § 119 to U.S. Provisional Patent Application No. 63/338,954, filed May 6, 2022 and titled "LYME RELATED INFECTION INDICATOR," the content of which is incorporated herein by reference in its entirety.

FIELD

Methods for identifying indications for testing for Lyme related infection.

BACKGROUND

The early diagnosis and detection of Lyme disease remains a challenge. Since Lyme disease is "The Great Mimicker," symptoms appearing similar to other systemic and neurological conditions often cause the correct diagnosis to be missed or delayed. Lack of diagnosis and treatment in the acute phase may result in a chronic and even neurological advancement in the undiagnosed disease.

The literature is sparse concerning the consequences and effect of Lyme related disease to vision, retinal changes, and the vascular network within the eyes. It is common for individuals to experience visual symptoms (e.g., fluctuation in vision, difficulty with reading/near work, light sensitivity, reduced convergence, pulling sensation behind eyes, floaters, etc.) from Tick-borne disease.

The eye has a rich vascular supply that ranges from small to medium sized blood vessels. The deeper capillary network of the inner layers of the retina is the radial peri-papillary capillary plexus. This network is responsible for supplying the densely packed nerve fiber layer.

Ischemia surrounding the optic nerve head (i.e., peri-papillary ischemia) is not a common finding in younger and middle-aged patients. Peri-papillary ischemia is age-related and more prevalent with persons over 60 years of age.

The central retinal artery diameter is approximately 160 μm. The peri-papillary capillaries are about 15 μm in diameter. A spirochete is approximately 1 μm in diameter and can easily invade the capillary plexus of the inner retina. Spirochetes can lead to formation of a biofilm as large as 50 μm. The capillaries of the radial peri-papillary plexus, being approximately 15 μm in diameter, are too narrow to permit passage of the biofilm. This can potentially lead to blockage and ischemia.

SUMMARY

Disclosed herein are methods for identifying indications for screening and/or testing for Lyme related infection. As noted above, peri-papillary ischemia is age related and thus not commonly found in younger and middle-aged individuals. In a study conducted involving individuals ages 6 to 60, pery-papillary ischemia was observed in a significant number of the test subjects who were previously diagnosed with Lyme related disease.

A first aspect of the present disclosure relates to a method for identifying an indication for testing for Lyme related infection. The method of the first aspect comprises the steps of: with respect to a subject presenting a sudden onset of at least one visual symptom known to be associated with Lyme related infection, screening the subject for peri-papillary ischemia; and if peri-papillary ischemia is present, recommending the subject undergo further testing for Lyme related infection.

In some embodiments of the first aspect of the present disclosure, the at least one visual symptom is selected from the group consisting of photophobia, visual fatigue, eye strain, loss of place, seeing print move on a page when reading, double vision, headaches, and combinations of two or more thereof.

In some embodiments of the first aspect of the present disclosure, screening the subject for peri-papillary ischemia comprises performing at least one optical observation of an optic nerve of the subject.

In some embodiments of the first aspect of the present disclosure, performing the at least one optical observation comprises performing at least one of fundus photography, direct ophthalmoscopy, and indirect ophthalmoscopy.

In some embodiments of the first aspect of the present disclosure, screening the subject for peri-papillary ischemia comprises performing ocular coherence tomography with angiography (OCT-A).

In some embodiments of the first aspect of the present disclosure, screening the subject for pen-papillary ischemia comprises partitioning an image of a pen-papillary area of the subject into quadrants, determining a vessel density for each quadrant, determining a total vessel density by calculating a sum of the vessel densities of the quadrants, determining a normalized vessel density for a healthy eye with no vessel atrophy, and determining a vessel atrophy of the peri-papillary area of the subject based on the total vessel density and the normalized vessel density.

In some embodiments of the first aspect of the present disclosure, the method further comprises determining the subject has peri-papillary ischemia when the vessel atrophy is at least about 30%.

In some embodiments of the first aspect of the present disclosure, the subject is below the age of about 50 years old.

In some embodiments of the first aspect of the present disclosure, the subject is between the age of about 1 years old and about 50 years old.

In some embodiments of the first aspect of the present disclosure, the method further comprises, if peri-papillary ischemia is present, further testing the subject for Lyme related infection.

In some embodiments of the first aspect of the present disclosure, the further testing comprises testing the subject for one or more of an *Anaplasma* infection, a *Babesia* infection, a *Bartonella* infection, *Borrelia* infection, a *Coxiella* infection, an *Ehrlichia* infection, a Flavivirus infection, a *Francisella* infection, a *Mycoplasma* infection, a Reoviridae infection, and a *Rickettsia* infection.

In some embodiments of the first aspect of the present disclosure, the further testing comprises testing the subject for one or more of an *Anaplasma phagocytophilum* infection, a *Babesia duncani* infection, a *Babesia microti* infection, a *Bartonella henselae* infection, a *Bartonella quintana* infection, a *Borrelia burgdorferi* infection, a *Borrelia hermsii* infection, a *Borrelia lonestari* infection, a *Borrelia parkeri* infection, a *Borrelia turicata* infection, a *Coxiella burnetii* infection, an *Ehrlichia chaffeensis* infection, an *Ehrlichia ewingii* infection, an *Ehrlichia muris* eauclairensis infection, a Flavivirus infection, a *Francisella tularensis* infection, a Reoviridae infection, and a *Rickettsia rickettsia* infection.

In some embodiments of the first aspect of the present disclosure, the method further comprises, if the subject has Lyme related infection, treating the Lyme related infection of the subject.

A second aspect of the present disclosure relates to a method for identifying an indication for testing for Lyme related infection. The method of the second aspect comprises the steps of: with respect to a subject presenting a sudden onset of at least one visual symptom known to be associated with Lyme related infection, screening the subject for peri-papillary ischemia using ocular coherence tomography angiography (OCT-A); and if peri-papillary ischemia is present, recommending the subject undergo further testing for Lyme related infection.

In some embodiments of the second aspect of the present disclosure, the at least one visual symptom is selected from the group consisting of photophobia, visual fatigue, eye strain, loss of place, seeing print move on a page when reading, double vision, headaches, and combinations of two or more thereof.

In some embodiments of the second aspect of the present disclosure, screening the subject for peri-papillary ischemia comprises partitioning an image of a peri-papillary area of the subject into quadrants, determining a vessel density for each quadrant, determining a total vessel density by calculating a sum of the vessel densities of the quadrants, determining a normalized vessel density for a healthy eye with no vessel atrophy, and determining a vessel atrophy of the peri-papillary area of the subject based on the total vessel density and the normalized vessel density.

In some embodiments of the second aspect of the present disclosure, the method further comprises determining the subject has peri-papillary ischemia when the vessel atrophy is at least about 30%.

In some embodiments of the second aspect of the present disclosure, the subject is below the age of about 50 years old.

In some embodiments of the second aspect of the present disclosure, the subject is between the age of about 1 years old and about 50 years old.

In some embodiments of the second aspect of the present disclosure, the method further comprises, if peri-papillary ischemia is present, further testing the subject for Lyme related infection.

In some embodiments of the second aspect of the present disclosure, the further testing comprises testing the subject for one or more of an *Anaplasma* infection, a *Babesia* infection, a *Bartonella* infection, *Borrelia* infection, a *Coxiella* infection, an *Ehrlichia* infection, a Flavivirus infection, a *Francisella* infection, a *Mycoplasma* infection, a Reoviridae infection, and a *Rickettsia* infection.

In some embodiments of the second aspect of the present disclosure, the further testing comprises testing the subject for one or more of an *Anaplasma phagocytophilum* infection, a *Babesia duncani* infection, a *Babesia microti* infection, a *Bartonella henselae* infection, a *Bartonella quintana* infection, a *Borrelia burgdorferi* infection, a *Borrelia hermsii* infection, a *Borrelia lonestari* infection, a *Borrelia parkeri* infection, a *Borrelia turicata* infection, a *Coxiella burnetii* infection, an *Ehrlichia chaffeensis* infection, an *Ehrlichia ewingii* infection, an *Ehrlichia muris* eauclairensis infection, a Flavivirus infection, a *Francisella tularensis* infection, a Reoviridae infection, and a *Rickettsia rickettsia* infection.

In some embodiments of the second aspect of the present disclosure, the method further comprises, if the subject has Lyme related infection, treating the Lyme related infection of the subject.

BRIEF DESCRIPTION OF DRAWINGS

For a more complete understanding of the present disclosure, reference is now made to the following description taken in conjunction with the accompanying drawings.

FIG. 1A is a fundus photograph of a right eye presented without filter. FIG. 1B is a fundus photograph of the left eye presented without filter. FIG. 1C is a fundus photograph of the right eye presented with a red-free filter. FIG. 1D is a fundus photograph of the left eye presented with a red-free filter.

FIGS. 2A through 2D are fundus photographs for a subject in a control group. FIG. 2A is a fundus photograph of a right eye presented without filter. FIG. 2B is a fundus photograph of the left eye presented without filter. FIG. 2C is a fundus photograph of the right eye presented with a red-free filter. FIG. 2D is a fundus photograph of the left eye presented with a red-free filter.

FIG. 3A is an OCT-A scan of a right eye of a subject in the experimental group. FIG. 3B is an OCT-A scan of a left eye of the subject in the experimental group. FIG. 3C is an OCT-A scan of a right eye of a subject in the control group. FIG. 3D is an OCT-A scan of a left eye of the subject in the control group.

DETAILED DESCRIPTION

Figures 1A, 1B, 1C, 1D:
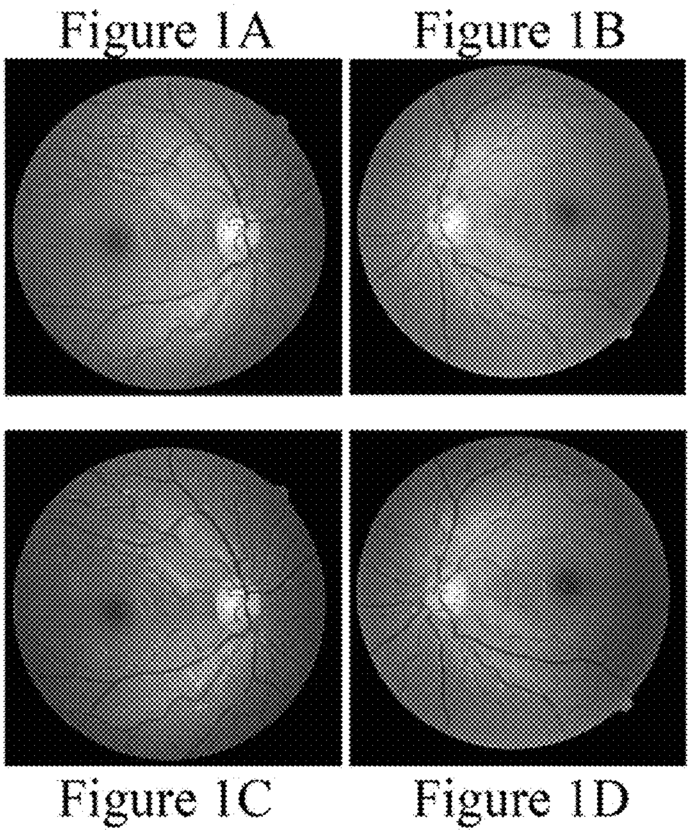
FIGS. 1A through 1D are fundus photographs for a subject in an experimental group.

Methods for Identifying Indications for Testing of Lyme Related Infection

The present disclosure provides methods for identifying indications for testing for Lyme related infection. In some embodiments, a method of the present disclosure comprises screening a subject, presenting a sudden onset of at least one visual symptom known to be associated with Lyme related infection, for peri-papillary ischemia and, if peri-papillary ischemia is present, recommending the subject undergo further testing for Lyme related infection. In other words, embodiments of the present disclosure involve recommending a subject undergo testing for Lyme related infection when it is determined the subject has peri-papillary ischemia and simultaneously is presenting a sudden onset of at least one visual symptom known to be associated with Lyme related infection.

In some embodiments, screening the subject for peri-papillary ischemia may comprise performing at least one optical observation of an optic nerve of the subject. In some embodiments, performing the at least one optical observation may comprise performing at least one of fundus photography, direct ophthalmoscopy, and indirect ophthalmoscopy.

In some embodiments, screening the subject for peri-papillary ischemia may comprise performing optical coherence tomography angiography (OCT-A).

In some embodiments, screening the subject for peri-papillary ischemia may comprise performing at least one optical observation (e.g., at least one of fundus photography, direct ophthalmoscopy, and indirect ophthalmoscopy) and OCT-A.

In some embodiments, screening the subject for peri-papillary ischemia comprises partitioning an image of a peri-papillary area (i.e., the 3 mm papillary region around the optic disc) of the subject's eye into quadrants, determining a vessel density for each quadrant (e.g., a first vessel density for a first quadrant, a second vessel density for a second quadrant, a third vessel density for a third quadrant, and a fourth vessel density for a fourth quadrant), determining a total vessel density by calculating a sum of the vessel densities of the quadrants (e.g., a sum of the vessel densities of the first, second, third, and fourth quadrants), determining a normalized vessel density for a healthy eye with no vessel atrophy, and determining a vessel atrophy of the peri-papillary area of the subject's eye based on the total vessel density and the normalized vessel density.

Determining the vessel density for each quadrant may be performed in various manners. OCT-A passes a beam of light into the tissue of the eye. In the OCT-A context, knowing the distance from the instrument and the width and depth of the beam at the projected distance, the reflected light off the surfaces of the vessels may be calculated into vessel density.

As noted above, screening for peri-papillary ischemia may comprise determining a normalized vessel density for a healthy eye with no vessel atrophy. Norms for vessel atrophy of a healthy eye have been established and are within the knowledge of one skilled in the art.

In some embodiments, determining the vessel atrophy of the peri-papillary area of the subject's eye may comprise calculating vessel atrophy as a percentage by dividing the total vessel density by the normalized vessel density, and multiplying the resultant by 100.

In some embodiments, determining peri-papillary ischemia is present may comprise determining the vessel atrophy of the peri-papillary area to be at least about 30%. In some embodiments, determining peri-papillary ischemia is present may comprise determining the vessel atrophy of the peri-papillary area to be at least about 35%. In some embodiments, determining peri-papillary ischemia is present may comprise determining the vessel atrophy of the peri-papillary area to be at least about 40%. In some embodiments, determining peri-papillary ischemia is present may comprise determining the vessel atrophy of the peri-papillary area to be at least about 45%. In some embodiments, determining peri-papillary ischemia is present may comprise determining the vessel atrophy of the peri-papillary area to be at least about 50%. In some embodiments, determining peri-papillary ischemia is present may comprise determining the vessel atrophy of the peri-papillary area to be at least about 55%. In some embodiments, determining peri-papillary ischemia is present may comprise determining the vessel atrophy of the peri-papillary area to be at least about 60%. In some embodiments, determining peri-papillary ischemia is present may comprise determining the vessel atrophy of the peri-papillary area to be at least about 65%. In some embodiments, determining peri-papillary ischemia is present may comprise determining the vessel atrophy of the peri-papillary area to be at least about 70%. In some embodiments, determining peri-papillary ischemia is present may comprise determining the vessel atrophy of the peri-papillary area to be at least about 75%. In some embodiments, determining peri-papillary ischemia is present may comprise determining the vessel atrophy of the peri-papillary area to be at least about 80%. In some embodiments, determining peri-papillary ischemia is present may comprise determining the vessel atrophy of the peri-papillary area to be at least about 85%. In some embodiments, determining peri-papillary ischemia is present may comprise determining the vessel atrophy of the peri-papillary area to be at least about 90%. In some embodiments, determining peri-papillary ischemia is present may comprise determining the vessel atrophy of the peri-papillary area to be at least about 95%.

According to some embodiments of the present disclosure, if peri-papillary ischemia is present, a method of the present disclosure may further comprise further testing the subject for Lyme related infection. Specific, illustrative Lyme related infections that may be tested for are described herein below under the heading "Lyme Related Infection".

Testing of Lyme related infection is within the knowledge of one skilled in the art. The present disclosure is not limited to any particular Lyme related infection testing methodology. As a non-limiting example, as of the filing of this disclosure, the Centers for Disease Control and Prevention (CDC) recommends a two-step testing process for Lyme disease, with both steps being performable with the same blood sample. The first step involves an enzyme immunoassay or an immunofluorescence assay. If the assay results are negative, it may be concluded that the subject does not have Lyme related infection. If, however, the assay results are positive, the second step of the testing is performed. The exact second step performed depends on the duration the subject has been experiencing symptoms. If the symptoms have been occurring for less than or equal to 30 days, an Immunoglobulin M (IgM) Western Blot and Immunoglobulin G (IgG) Western Blot is performed. Conversely, if the symptoms have been occurring for more than 30 days, just an IgG Western Blot is performed.

Moreover, according to some embodiments of the present disclosure, if the further testing indicates the subject has Lyme related infection, a method of the present disclosure may further comprise treating the Lyme related infection of the subject. Treating Lyme related infection is within the knowledge of one skilled in the art. The present disclosure is not limited to any particular Lyme related infection treatment methodology. Illustrative Lyme related infection treatment methodologies are described herein below under the heading "Treatment of Lyme Related Infection".

Subjects

As used herein, a "subject" refers to a human or vertebrate mammal including but not limited to a dog, cat, horse, goat, cow, sheep, rodent, and primate (e.g., monkey). Thus, the present disclosure can be used to identify indications for testing for Lyme related infection in human and non-human subjects. For instance, methods of the present disclosure can be used in veterinary applications as well as in human prevention and treatment regimens.

In some embodiments, the subject may be below the age of about 50 years old. In some embodiments, the subject may be below the age of about 45 years old. In some embodiments, the subject may be below the age of about 40 years old. In some embodiments, the subject may be below the age of about 35 years old. In some embodiments, the subject may be below the age of about 30 years old. In some embodiments, the subject may be below the age of about 25 years old. In some embodiments, the subject may be below the age of about 20 years old. In some embodiments, the subject may be below the age of about 15 years old. In some embodiments, the subject may be below the age of about 10 years old. In some embodiments, the subject may be below the age of about 5 years old.

In some embodiments, the subject may be a human below the age of about 50 years old. In some embodiments, the subject may be a human below the age of about 45 years old. In some embodiments, the subject may be a human below the age of about 40 years old. In some embodiments, the subject may be a human below the age of about 35 years old. In some embodiments, the subject may be a human below the age of about 30 years old. In some embodiments, the subject may be a human below the age of about 25 years old. In some embodiments, the subject may be a human below the age of about 20 years old. In some embodiments, the subject may be a human below the age of about 15 years old. In some embodiments, the subject may be a human below the age of about 10 years old. In some embodiments, the subject may be a human below the age of about 5 years old.

In some embodiments, the subject may be between the age of about 1 years old and about 50 years old. In some embodiments, the subject may be between the age of about 5 years old and about 50 years old. In some embodiments, the subject may be between the age of about 10 years old and about 50 years old. In some embodiments, the subject may be between the age of about 15 years old and about 50 years old. In some embodiments, the subject may be between the age of about 20 years old and about 50 years old. In some embodiments, the subject may be between the age of about 25 years old and about 50 years old. In some embodiments, the subject may be between the age of about 30 years old and about 50 years old. In some embodiments, the subject may be between the age of about 35 years old and about 50 years old. In some embodiments, the subject may be between the age of about 40 years old and about 50 years old. In some embodiments, the subject may be between the age of about 45 years old and about 50 years old.

In some embodiments, the subject may be between the age of about 1 years old and about 45 years old. In some embodiments, the subject may be between the age of about 1 years old and about 40 years old. In some embodiments, the subject may be between the age of about 1 years old and about 35 years old. In some embodiments, the subject may be between the age of about 1 years old and about 30 years old. In some embodiments, the subject may be between the age of about 1 years old and about 25 years old. In some embodiments, the subject may be between the age of about 1 years old and about 20 years old. In some embodiments, the subject may be between the age of about 1 years old and about 15 years old. In some embodiments, the subject may be between the age of about 1 years old and about 10 years old. In some embodiments, the subject may be between the age of about 1 years old and about 5 years old.

In some embodiments, the subject may be a human between the age of about 1 years old and about 50 years old. In some embodiments, the subject may be a human between the age of about 5 years old and about 50 years old. In some embodiments, the subject may be a human between the age of about 10 years old and about 50 years old. In some embodiments, the subject may be a human between the age of about 15 years old and about 50 years old. In some embodiments, the subject may be a human between the age of about 20 years old and about 50 years old. In some embodiments, the subject may be a human between the age of about 25 years old and about 50 years old. In some embodiments, the subject may be a human between the age of about 30 years old and about 50 years old. In some embodiments, the subject may be a human between the age of about 35 years old and about 50 years old. In some embodiments, the subject may be a human between the age of about 40 years old and about 50 years old. In some embodiments, the subject may be a human between the age of about 45 years old and about 50 years old.

In some embodiments, the subject may be a human between the age of about 1 years old and about 45 years old. In some embodiments, the subject may be a human between the age of about 1 years old and about 40 years old. In some embodiments, the subject may be a human between the age of about 1 years old and about 35 years old. In some embodiments, the subject may be a human between the age of about 1 years old and about 30 years old. In some embodiments, the subject may be a human between the age of about 1 years old and about 25 years old. In some embodiments, the subject may be a human between the age of about 1 years old and about 20 years old. In some embodiments, the subject may be a human between the age of about 1 years old and about 15 years old. In some embodiments, the subject may be a human between the age of about 1 years old and about 10 years old. In some embodiments, the subject may be a human between the age of about 1 years old and about 5 years old.

Sudden Onset of Visual Symptoms Associated with Lyme Related Infection

As disclosed herein, in some embodiments only a subject exhibiting a sudden onset of visual symptoms may be screened for peri-papillary ischemia. As used herein, "sudden onset of symptoms" refers to symptoms that develop quickly. Sudden onset symptoms can change over time, worsen rapidly, and be severe. Sudden onset symptoms are sometimes referred to as quick onset symptoms or acute symptoms. Sudden onset symptoms are to be contrasted with symptoms that develop slowly over a period of time, which are called chronic symptoms.

As disclosed herein, in some embodiments only a subject exhibiting a sudden onset of visual symptoms, known to be associated with Lyme related infection, may be screened for peri-papillary ischemia. Examples of visual symptoms known to be associated with Lyme related infection include, but are not limited to, photophobia (i.e., extreme sensitivity to light), visual fatigue (also known as eye fatigue, and which may manifest as headaches, blurred or reduced vision, dry eye, difficulty maintaining visual focus, and eye pain), eye strain, loss of place, seeing print move on a page when reading, double vision (i.e., diplopia), and headaches. In some embodiments, a subject, presenting a sudden onset of one of the foregoing visual symptoms known to be associated with Lyme related infection, may be screened for peri-papillary ischemia. In some embodiments, a subject, presenting a sudden onset of two or more of the foregoing visual symptoms known to be associated with Lyme related infection, may be screened for peri-papillary ischemia.

Peri-Papillary Ischemia

Each eye of an animal has an optic nerve, which is a bundle of nerve fibers that carry visual messages from the eye to the brain. The optic nerve head (i.e., where the optic nerve connects to the back of the eye at the retina) has a highly vascular network of blood vessels within the eye.

Peri-papillary ischemia is a loss (or atrophy) of density of the blood vessels of the optic nerve head. Peri-papillary ischemia occurs when blood does not flow properly to the optic nerve. A common symptom of peri-papillary ischemia is a transient ischemic attack, (i.e., a darkening of vision for a few seconds or minutes followed by a return to normal vision). Peri-papillary ischemia often occurs in individuals at least 50 years old.

Fundus Photography

Fundus photography is an optical technique that may be used in diagnosing peri-papillary ischemia. Fundus photography involves taking one or more images of the interior of the eye through the pupil using a fundus camera. A fundus camera is a low-power microscope attached to a camera. The optical design of the fundus camera is based on the indirect ophthalmoscope. A fundus camera is described by angle of view. A typical fundus camera has an angle of 30°, which creates a film image 2.5 times larger than life.

Light, generated from a viewing lamp or an electronic flash, is projected through a set of filters and onto a round mirror, which reflects the light into a series of lenses that focus the light. A mask on the uppermost lens shapes the light into a donut shaped light, which is reflected onto a round mirror with a central aperture, exits the camera through the lens, and proceeds into the eye via the cornea. The resulting retinal image exits the cornea through the central, un-illuminated portion of the doughnut, continues through the central aperture of the aforementioned mirror, through an astigmatic correction device and diopter compensation lenses, and back to the lens reflect camera system.

In some instances, an eye drop may be administered, prior to taking the images, in order to increase the size of the pupil, thereby allowing examination of the interior of the eye more easily. Typically, the subject undergoing a fundus photography examination is instructed to rest the subject's chin on a chin rest of the fundus camera, and place the subject's forehead against a bar on the fundus camera. Then, the fundus camera may be focused and aligned on the pupil of the subject's eye, and the one or more images may be taken.

Direct Ophthalmoscopy

Direct ophthalmoscopy is another optic technique usable in diagnosing peri-papillary ischemia. The principle of direct ophthalmoscopy is that, if the subject's eye is emmetropic (i.e., does not have any refractive errors, such as nearsightedness (myopia), farsightedness (hyperopia), or astigmatism), light rays emanating from a point on the fundus (i.e., the part of the eye, that is the retina, that is farthest from the opening, that is the cornea) emerge as a parallel beam. If the beam enters the pupil of an emmetropic observer, the parallel rays are focused on the observer's retina and form an image of the subject's retina on the observer's retina.

Direct ophthalmoscopy utilizes a direct ophthalmoscope. A direct ophthalmoscope includes an incandescent lamp for sending light to the subject's eye. The direct ophthalmoscope also includes a viewing aperture through which the operator looks. A small, tilted (e.g., 45°) mirror is placed just beneath and adjacent the viewing aperture. The direct ophthalmoscope also have two wheels, one enabling the operator to adjust diameter, shape, and color of the illumination beam, and the other usable to insert "compensating" lenses behind the viewing aperture.

While the subject is seated in a dark room, the observer positions the direct ophthalmoscope so it is level with the subject's eye. The observer also instructs the subject to focus on an object straight ahead of the subject (e.g., a wall). To examine the subject's right eye, the observer holds the direct ophthalmoscope in the observer's right hand and uses the observer's right eye to look through the viewing aperture of the direct ophthalmoscope. The observer also places the observer's left hand on the subject's head and the observer's left thumb on the subject's right eyebrow. The observer then positions the direct ophthalmoscope about 1-2 inches from the subject's right eye and about 15 degrees to the right of the subject. Once the observer finds a red reflex, the observer may move closer until the optic nerve is viewable, at which point the observer may rotate the diopter lens until the optic nerve comes into focus. The observer may then scan slightly up, down, right, and left to look at the peri-papillary vessels to determine whether peri-papillary ischemia is present.

Indirect Ophthalmoscopy

Indirect ophthalmoscopy is a further optic technique usable in diagnosing peri-papillary ischemia. An indirect ophthalmoscope is worn on the observer's head, or may be attached to the observer's eyewear, and is used to inspect the fundus, or back of the eye. An indirect ophthalmoscope produces a stereoscopic image with between 2 to 5 times magnification.

In operation, the observer orients the indirect ophthalmoscope so the light, from an internal light source thereof (e.g., a halogen bulb or light emitting diode (LED)), is directed into the subject's eye. The observer holds a positive-powered condensing lens at a focal length from the subject's eye. This lens condenses light from the illumination system towards the subject's pupil. Light reflected from the retina passes back through the lens, thereby creating a horizontally and laterally inverted image of the fundus. The viewing system of the indirect ophthalmoscope includes a pair of low-powered convex lenses.

A +20 D lens is the standard lens for general examination, offering 3 times magnification and a field of view of approximately 45°. A +30 D lens offers 2 times magnification along with a field of view of approximately 65°. A 90° diopter lens may also be used to observe the optic nerve.

Optical Coherence Tomography (OCT) Angiography

Optical coherence tomography angiography (OCT-A) is yet another technique for diagnosing peri-papillary ischemia. OCT-A is a technique for imaging the microvasculature of the retina and the choroid. OCT-A uses laser light reflectance of the surface of moving red blood cells to depict vessels through segments of the eye. OCT-A eliminates the need for intravascular dyes.

The OCT scan of a subject's retina includes multiple individual A-scans. A-scans are compiled into a B-scan, which provides cross-sectional structural information. Using OCT-A, the same tissue area may be repeatedly images, and differences may be analyzed between scans, thereby allowing for detection of zones containing high flow rates and zones with slower flow rates, or no flow at all.

Light is emitted through either a spectral domain OCT or a swept-source OCT. Spectral domain OCT has a wavelength near 800 nm. By contrast, swept-source OCT utilized a longer wavelength, close to 1050 nm. Generally, longer wavelengths have a deeper tissue penetration, but a lower axial resolution.

OCT-A utilizes two methods for motion detection: amplitude decorrelation or phase variance. Amplitude decorrelation detects differences in amplitude between two different OCT B-scans. Phase variance, in contrast, is related to the emitted light wave properties, and the variation of phase when intercepting moving objects. Split spectrum amplitude decorrelation and volume averaging may be used to improve visualization and reduce background noise from normal small eye movements. These OCT-A algorithms produce an image (e.g., 3 $mm^2$ to 12 $mm^2$) that is segmented into four zones: the superficial retinal plexus, the deep retinal plexus, the outer retina, and the choriocapillaris.

Lyme Related Infection

Lyme related infection is spread to humans via bites from infected ticks. Lyme related infection, if left untreated, can spread to a human's heart, joints, and nervous system. Traditionally, Lyme related infection has been diagnosed based on symptoms (e.g., fever, shills, aches, and pains), physical manifestations (e.g., rash), and the likelihood of exposure to infected ticks.

As used herein, "Lyme related infection" refers to Lyme disease and related coinfections such as, but not limited to, babesiosis, ehrlichiosis, Colorado tick fever, tick-borne relapsing fever, Q fever, powassan viral encephalitis, Rocky Mountain spotted fever, tick paralysis, tularemia, and *bartonella.*

Lyme disease, sometimes referred to as STARI or Masters' Disease, is commonly found in deer ticks, pacific black-legged ticks, and lone star ticks. Lyme disease is caused by the bacterium *Borrelia burgdorferi* and *Borrelia lonestari* (and potentially other *Borrelia* bacteria). Common symptoms of Lyme disease are a red "bull's-eye" rash, fever, shills, headache, fatigue, muscle and joint aches, and swollen lymph nodes.

Babesiosis is an infection of the red blood cells, and is typically associated with body aches, chills, fatigue, fever, headache, loss of appetite, sweating, and hemolytic anemia (a condition where red blood cells die faster than the body can produce new ones). Babesiosis has been identified as being caused by deer tick and pacific black-legged tick bites, and is known to be caused by *Babesia microti* and *Babesia duncani* (WA-1).

In the United States, ehrlichiosis is used to generally describe disease caused by *Anaplasma phagocytophilum* (formerly *Ehrlichia phagocytophilum*), *Ehrlichia chaffeensis, Ehrlichia ewingii*, or *Ehrlichia muris* eauclairensis. These bacteria have been observed to spread to human by deer ticks, pacific black-legged ticks, American dog ticks, and lone start ticks. People with ehrlichiosis often experience fever, chills, headache, muscle aches, and upset stomach.

Colorado tick fever is a viral disease spread by the bite of an infected Rocky Mountain wood tick. Common symptoms of Colorado tick fever include fever, chills, headache, body aches, and fatigue. In some situations, an individual may experience a biphasic fever. Colorado tick fever is caused by a virus of the family Reoviridae, subfamily, Spinareovirinae, genus Coltivirus.

Tick-borne relapsing fever is a bacterial infection spread by the tick species *Ornithodoros hermsi, Ornithordoros parkeri*, and *Ornithorodoros turicata*. The main symptom of tick-borne relapsing fever are high (recurring) fever (e.g., 103° F.), petechial rash, headache, and muscle and joint aches. Several *Borrelia* species are known to cause tick-borne relapsing fever. Such species include *Borrelia hermsii, Borrelia parkeri*, and *Borrelia turicata.*

Q fever typically manifests as a fever, chills or sweats, fatigue, headache, muscle aches, nausea, vomiting, or diarrhea, chest pain, stomach pain, weight loss, and non-productive cough. The causative agent for Q fever is *Coxiella burnetii*. Q fever is known to be spread by bites from brown dog ticks, Rocky Mountain ticks, and lone star ticks.

Powassan viral encephalitis is a brain infection that can result from the bite of a woodchuck tick. Initial symptoms includes fever, headache, vomiting, and weakness, with later onset sever symptoms includes confusion, loss of coordination, difficulty speaking, weakness of the arms or legs, and seizures. The causative agent of Powassan viral encephalitis is the genus Flavivirus.

Rocky Mountain spotted fever is often contracted through a bite from an American dog tick or Rocky Mountain wood tick. Early symptoms of Rocky Mountain spotted fever are high fever, severe headache, malaise, myalgia, edema around the eyes and on the back of hands, and gastrointestinal symptoms (e.g., nausea, vomiting, and anorexia). The causative agent of Rocky Mountain spotted fever is *Rickettsia*, for example *Rickettsia rickettsii.*

Tick paralysis is often contracted through a bite from an American dog tick, a Rocky Mountain wood tick, or a lone star tick. The causative agent of tick paralysis is a neurotoxin excreted from a tick's salivary gland (e.g., while the tick hangs on to its host for several days). Common symptoms of tick paralysis are fatigue, flaccid paralysis, tongue and facial paralysis, and convulsions.

Tularemia can be contracted through a bite from an American dog tick, Rocky Mountain tick, or lone star tick. Common symptoms of tularemia are indolent ulcers and swollen lymph nodes. A known causative agent of tularemia is *Francisella tularensis.*

*Bartonella* is a bacterial infection that can be contracted from cats, ticks, and fleas. Common symptoms include fever, mild neurologic signs, granulomatous lymphadenitis, and skin lesions. The causative agents of a *bartonella* bacterial infection is the *Bartonella* bacteria, several species of which include *Bartonella quintana* and *Bartonella henselae.*

In some embodiments, if peri-papillary is present in the subject, the subject may be further tested for one or more of an *Anaplasma* infection, a *Babesia* infection, a *Bartonella* infection, *Borrelia* infection, a *Coxiella* infection, an *Ehrlichia* infection, a Flavivirus infection, a *Francisella* infection, a *Mycoplasma* infection, a Reoviridae infection, and a *Rickettsia* infection.

In some embodiments, if peri-papillary is present in the subject, the subject may be further tested for one or more of an *Anaplasma phagocytophilum* infection, a *Babesia duncani* infection, a *Babesia microti* infection, a *Bartonella henselae* infection, a *Bartonella quintana* infection, a *Borrelia burgdorferi* infection, a *Borrelia hermsii* infection, a *Borrelia lonestari* infection, a *Borrelia parkeri* infection, a *Borrelia turicata* infection, a *Coxiella burnetii* infection, an *Ehrlichia chaffeensis* infection, an *Ehrlichia ewingii* infection, an *Ehrlichia muris* eauclairensis infection, a Flavivirus infection, a *Francisella tularensis* infection, a Reoviridae infection, and a *Rickettsia rickettsia* infection.

Treatment of Lyme Related Infection

As disclosed herein above, some embodiments of the present disclosure involve treating Lyme related infection of a subject. As used herein, the terms "treatment," "treat," and "treating" refer to reversing, alleviating, or inhibiting the progress of Lyme related infection.

Treatment of Lyme related infection may involve the administration of one or more compounds, or one or more pharmaceutical compositions thereof. As used herein, the terms "administer," "administering," and "administration" refer to implanting, absorbing, ingesting, injecting, inhaling, or otherwise introducing one or more compounds for treating Lyme related infection, or one or more pharmaceutical compositions thereof.

A dosage level for a compound for treating Lyme related infection, or a pharmaceutical composition thereof, is within the knowledge of one skilled in the art, or can be determined by one skill in the art using routine experimentation. A compound for treating Lyme related infection, or pharmaceutical composition thereof, may be administered to a subject in a pharmaceutically effective dose.

A variety of administration routes are available. The particular delivery mode selected will depend upon the particular condition being treated and the dosage required for therapeutic efficacy. Methods of this disclosure, generally speaking, may be practiced using any mode of administration that is medically acceptable, meaning any mode that produces effective levels of treatment without causing clinically unacceptable adverse effects. In some embodiments, a compound for treating Lyme related infection, or pharmaceutical composition thereof, may be administered via an oral, enteral, mucosal, percutaneous, and/or parenteral route. The term "parenteral" includes subcutaneous, intrathecal, intravenous, intramuscular, intraperitoneal, and intrasternal injection, as well as infusion techniques. Other routes include, but are not limited to, nasal (e.g., via a gastro-nasal tube), dermal, vaginal, rectal, and sublingual. Delivery routes of the present disclosure may include intrathecal, intraventricular, or intracranial. In some embodiments, a compound for treating Lyme related infection, or pharmaceutical composition thereof, may be placed within a slow release matrix and administered by placement of the matrix in the subject.

A compound for treating Lyme related infection, or pharmaceutical composition thereof, may be administered in a formulation, which may be administered in a pharmaceutically acceptable solution, which may routinely contain pharmaceutically acceptable concentrations of salt, buffering agents, preservatives, compatible carriers, adjuvants, and optionally other therapeutic ingredients.

According to methods of the present disclosure, Lyme related infection may be treated using a pharmaceutical composition. In general, a pharmaceutical composition is a composition comprising a pharmaceutically active ingredient and one or more pharmaceutically acceptable carrier. Pharmaceutically acceptable carriers are well known to the skilled artisan and may be selected and utilized using routine methods. As used herein, a pharmaceutically acceptable carrier means a non-toxic material that does not interfere with the effectiveness of the biological activity of the pharmaceutically active ingredient. Pharmaceutically acceptable carriers may include diluents, fillers, salts, buffers, stabilizers, solubilizers, and other materials that are well-known in the art.

In some embodiments, a method of the present disclosure may comprise treating the Lyme related infection of a subject using one or more commercially available medications. Example medications include Amoxicillin, Ceftriaxone, Cefuroxime, and Doxycycline.

EXAMPLES

Example 1. Study Determining Observed Peri Papillary Ischemia is a Biomarker of Lyme Related Infection

Method

This study was conducted using an experimental design that included subjects for an experimental and a control group. The experimental group included 20 subjects diagnosed with *Borrelia Burgdorferi* as the common denominator versus a cohort group with no history of tick-borne disease or related symptoms. Subjects were chosen between the ages of 8-40 years old. Subjects were provided a HIPAA compliant consent form for participation in the study. Parents or guardians signed this form for those under the age of 18 years old.

A standard history form was used to document symptoms and medical history. All subjects were required to have a diagnosis of Lyme related infection prior to testing by a physician. Lyme test results were collected for documentation to analyze any further patterns of subject symptoms and presentation.

Monocular and binocular corrected visual acuities were recorded using a Snellen chart for all subjects at distance (6 meters) and near distances (40 cm) followed by retinal photos and OCT-A of the optic nerve head. Retinal photos were taken using Nidek Non-Mydriatic Auto Focus Camera AFC-330. OCT-A was accomplished on all subjects using Optovue RTVue.

Fundus photos and OCT-A imaging of Lyme positive subjects were compared with healthy subjects to determine changes in the appearance of the retina along with comparison of retinal capillary bed in the deeper layer of the retina surrounding the optic nerve. The angiography provides a color-coded rating scale for evaluating vessel drop-out or vessel atrophy ($V_\alpha$). The rating scale ranged from 0% (red), or no drop-out, to 100% (blue) demonstrating the greatest amount of $V_\alpha$. This scale was used to assess changes in the $V_\alpha$ for the experimental group compared to the control group.

Intra-ocular pressure (TOP) was taken by applanation tonometry for all subjects and a careful assessment of the optic nerve to assess asymmetry between the peri-papillary ischemia.

Data Analysis

Fundus photographs of the optic nerves compare finding of peri-papillary ischemia for a subject in the experimental group (see FIGS. 1A through 1D) and a subject in the control group (see FIGS. 2A through 2D).

FIG. 1A is a fundus photograph of an experimental group subject's right eye presented without filter. FIG. 1B is a fundus photograph of the experimental group subject's left eye presented without filter. FIG. 1C is a fundus photograph of the experimental group subject's right eye presented with a red-free filter. FIG. 1D is a fundus photograph of the experimental group subject's left eye presented with a red-free filter.

FIG. 2A is a fundus photograph of a control group subject's right eye presented without filter. FIG. 2B is a fundus photograph of the control group subject's left eye presented without filter. FIG. 2C is a fundus photograph of the control group subject's right eye presented with a red-free filter. FIG. 2D is a fundus photograph of the control group subject's left eye presented with a red-free filter.

Data for vessel atrophy ($V_\alpha$) (also known as vessel drop-out) was used to evaluate statistical significance between the experimental and control groups. An OCT-A assessed vessel density of the superficial vascular complex, deep vascular complex, and radial peri-papillary capillaries for both groups. The OCT-A provides a graphic representation with corresponding change in color hue that demonstrates red scaling (0%) for no $V_\alpha$ and blue scaling (100%) for maximum $V_\alpha$ (see FIGS. 3A through 3D).

Figure 3A:
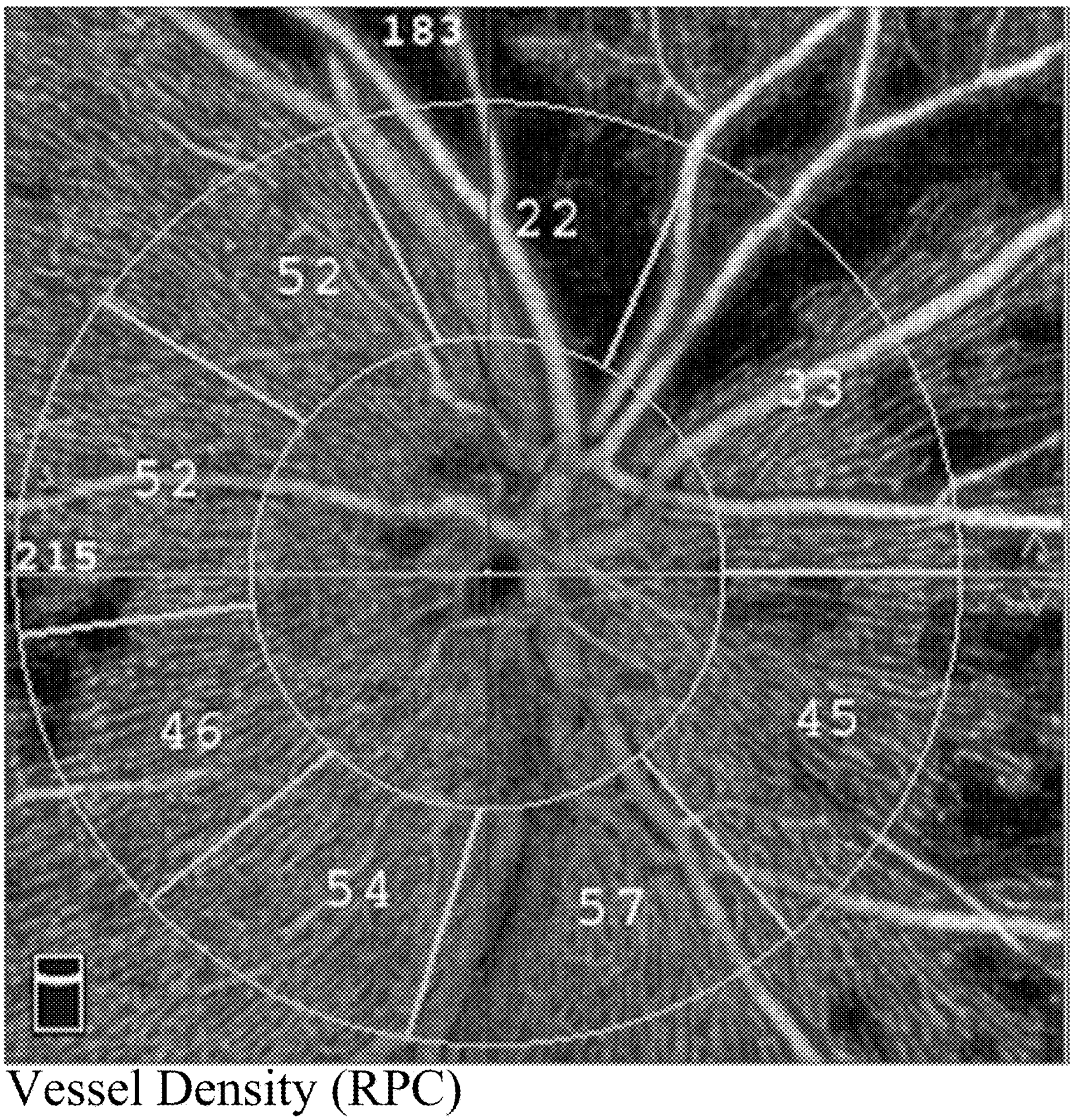
FIGS. 3A through 3D are Optical coherence tomography angiography (OCT-A) scans.
Figure 3B:
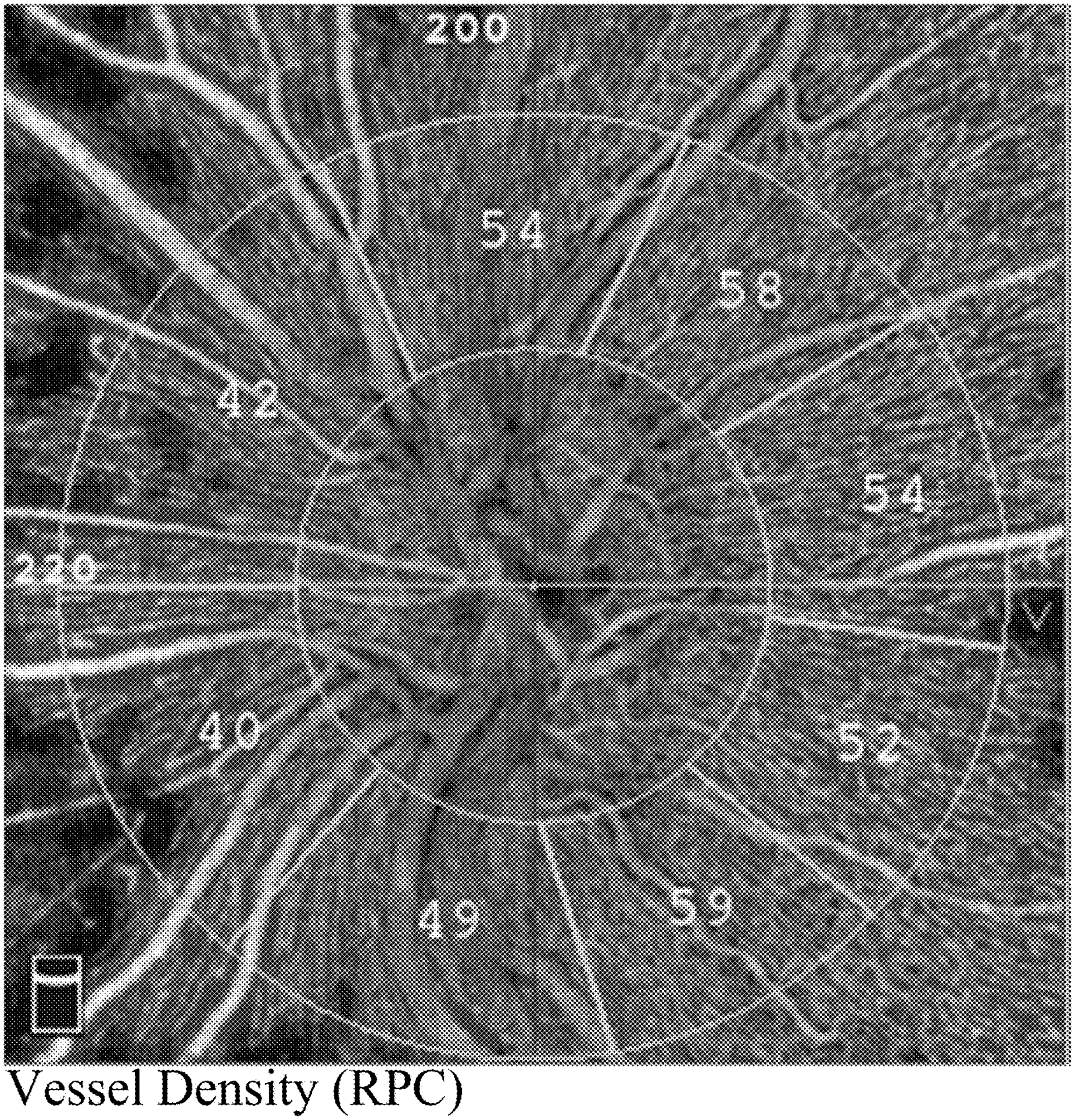
Figure 3C:
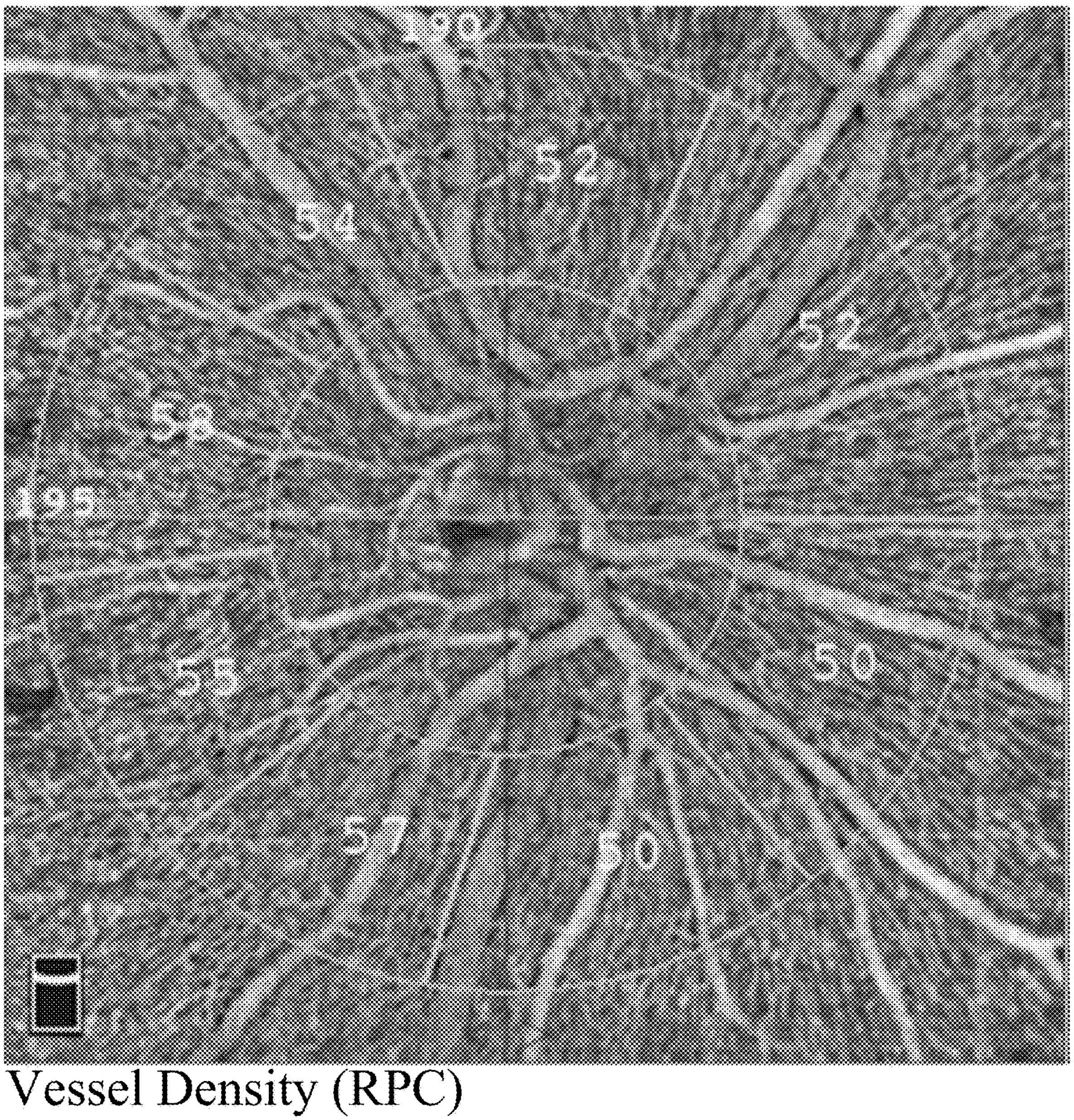
Figure 3D:
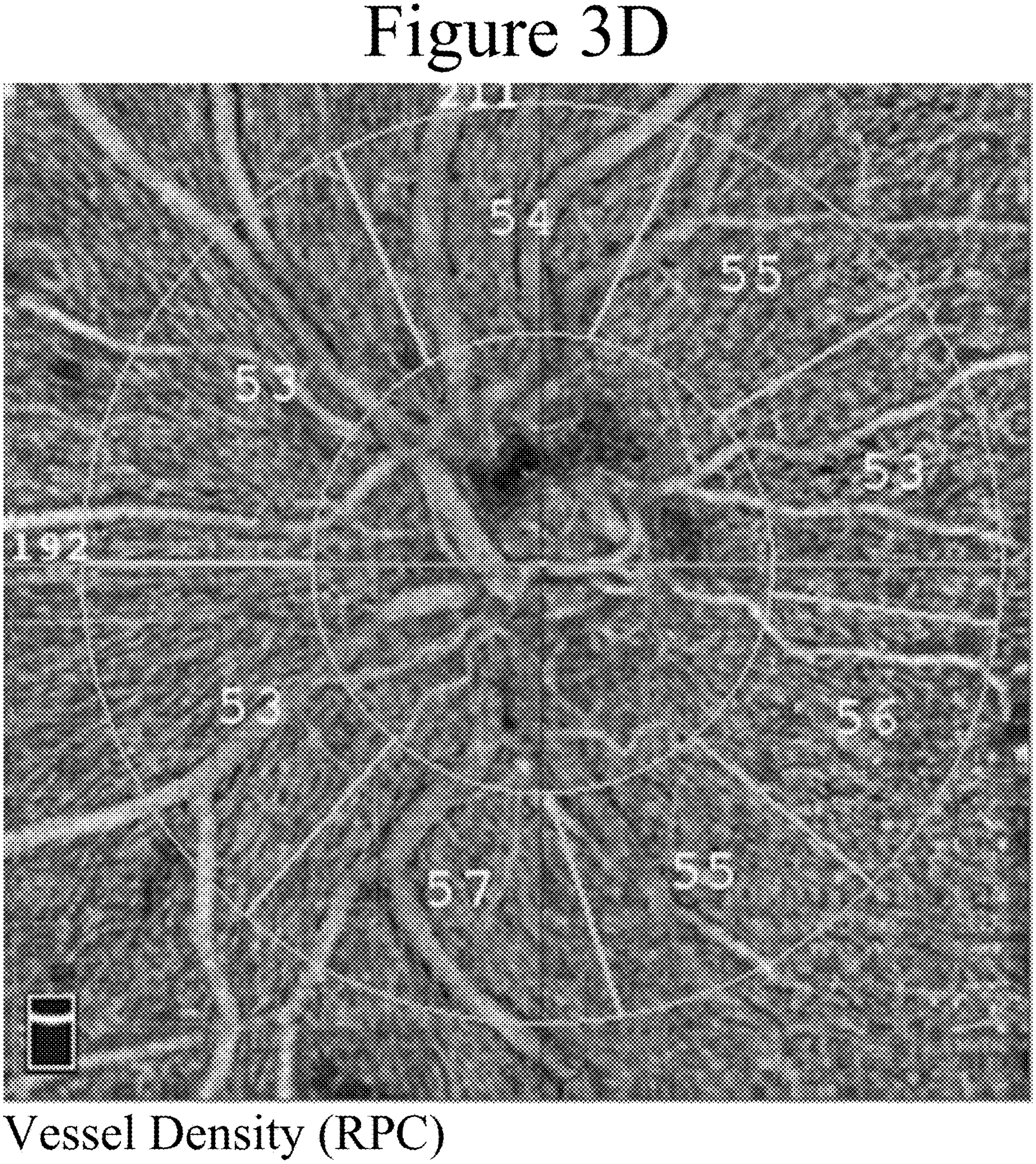

FIG. 3A is an OCT-A scan of a right eye of a subject in the experimental group. FIG. 3B is an OCT-A scan of a left eye of the subject in the experimental group. FIG. 3C is an OCT-A scan of a right eye of a subject in the control group. FIG. 3D is an OCT-A scan of a left eye of the subject in the control group.

An algorithm was developed to quantify vessel atrophy ($V_\alpha$). The normal density of vessels represents a value of 10. The reduction in density is then represented accordingly. An example would be if a quadrant showed 30% atrophy, the quantification would be represented as 7.

The algorithm may be demonstrated as:

$$V_d = \frac{S_R D}{S_N D} = V_a \quad \text{Equation 1}$$

where $V_d$ is vessel density, $S_RD$ is the summation of the quadrants' reduced densities, $S_ND$ is the summation of the quadrants' normal densities, and $V_\alpha$ is vessel atrophy.

Analysis utilized a two-tail t-test to compare unadjusted differences in main outcomes measures between each cohort at the 95% confidence level.

All testing was conducted at Padula Institute of Vision in Guilford, CT (USA). All testing was conducted by a technician trained in administering fundus photography and OCT-A.

Results

Twenty subjects were selected for each of the experimental and control groups. In the experimental arm, 11 subjects were female, compared to 14 subjects were female in the control group. The average age for subjects was 22 (experimental group) and 30 (control group). The average estimated time since onset of infection was 22 months for subjects in the experimental group. The age range for the experimental group was from 9-32 and for the control group 12-35 years of age.

TABLE 1

Demographics of the Experimental and Control Groups

| | Age range for selection | Average Age | Gender | Time from Onset of Infection |
|---|---|---|---|---|
| Experimental Group | 9-32 years | 22 | 11 Female<br>9 Male | 22 months |
| Control Group | 12-35 years | 30 | 14 Female<br>6 Male | N/A |

As represented in Table 2, there was a general reduction in distance visual acuity in the experimental group when compared to the control group.

TABLE 2

Bionocular distance visual acuities recorded for the experimental and control groups.

| | 20/20 to 20/25 Acuity | 20/30 to 20/60 Acuity | 20/80 or Greater Acuity |
|---|---|---|---|
| Experimental Group | 9 | 11 | 0 |
| Control Group | 16 | 4 | 0 |

As represented in Table 3, subjects in the experimental group included 15 infected with *Borrelia burgdorferi,* 8 with *Babesia,* 11 with *Bartonella,* 6 with *Ehrlichia*, and 4 with *Mycoplasma*.

TABLE 3

Number of subjects with tick-borne infection.

| | *Borrelia burgdorferi* | *Babesia* | *Bartonella* | *Ehrlichia* | *Mycoplasma* |
|---|---|---|---|---|---|
| Experimental Group | 15 | 8 | 11 | 6 | 4 |
| Control Group | N/A | N/A | N/A | N/A | N/A |

The control group was composed of subjects who had no active or past tick-borne infection. Subjects in the experimental group demonstrated difficulties with convergence and accommodation. Oculomotor difficulties, such as a jerky quality of eye movements during pursuit tracking and inability to sustain accurate saccadic fixations, were common characteristics. Subjects in the experimental group also showed reduced visual acuity and exophoria (i.e., tendency for the eyes to diverge as measured under bi-ocular conditions). The common symptoms of subjects in the experimental group were visual fatigue, seeing print or stationary objects in the environment appearing to move, headaches, difficulty with tolerating movement in their peripheral vision, brain fog, and a pulling sensation behind their eyes. Applanation tonometry found no increased TOP in either experimental or control groups. Assessment of the optic nerves on fundus photography showed no asymmetries of the cup-to-disc ratio or enlarged cups that could possibly indicate glaucoma in subjects in either the experimental or control groups.

Fundus photography demonstrated that for subjects in the experimental group, all showed a white ring or "halo" surrounding the optic nerve of peri-papillary ischemia compared to only one subject showing a mild state of peri-papillary ischemia in the control group (see FIGS. 1A through 1D). FIGS. 1A through 1D demonstrate an area of peri-papillary ischemia (subject in the experimental group) compared to FIGS. 2A through 2D showing no peri-papillary ischemia (subject in the control group).

The researchers also completed a careful assessment of the optic nerve head utilizing OCT-A. The evaluation consisted of measuring the color hue of the peri-papillary area surrounding the optic nerve head (ONH), overall size of the optic nerve, appearance of vessels around the ONH and the depth and insertion of the nerve. All of the subjects in the experimental group had some signs of peri-papillary ischemia surrounding the ONH. In comparison, only one subject in the control group showed peri-papillary ischemia. Subjects in both groups showed no other abnormal characteristics to indicate compromise of health to the optic nerve or surrounding area.

Table 4 shows the average calculated values of $V_\alpha$, between the experimental and control groups. It was determined that the experimental group generally showed an increased percentage of $V_\alpha$, compared to the control group. Careful assessment of both right and left eyes was conducted, and the average of both eyes was then used to determine overall $V_\alpha$, in each subject. The average $V_\alpha$, for the subjects in the experimental group was 49.594%, whereas the average $V_\alpha$ for subjects in the control group was 11.656%.

TABLE 4

Comparison of OCT-A vessel atrophy ($V_a$) [in percentage] for the experimental and control groups.

| Subject | Experimental Group % $V_a$ | Control Group % $V_a$ |
|---|---|---|
| 1 | 57.5 | 32.5 |
| 2 | 40 | 15 |
| 3 | 33.125 | 11.875 |
| 4 | 50 | 10 |
| 5 | 36.875 | 8.75 |
| 6 | 61.25 | 6.875 |
| 7 | 65 | 10 |
| 8 | 36.25 | 24.375 |
| 9 | 45.625 | 10 |
| 10 | 65 | 12.5 |
| 11 | 51.25 | 9.375 |
| 12 | 60 | 10 |
| 13 | 43.125 | 7.5 |
| 14 | 38.75 | 9.375 |
| 15 | 52.5 | 10 |
| 16 | 66.25 | 10.625 |
| 17 | 41.875 | 8.125 |
| 18 | 40 | 10 |
| 19 | 56.25 | 7.5 |
| 20 | 51.25 | 8.75 |

Analysis

A two-tailed t-test for dependent means was used to calculate the significance of the comparison of the percentage of $V_\alpha$ for the subjects in the experimental and control groups. As represented in Table 5, the mean for the experimental group was 49.59375 and the mean for the control group was 11.65625. The value oft was determined as 14.538305. The standard deviation for the experimental group was 10.361, and 6.168 for the control group. The result of this analysis is highly statistically significant at $p<0.001$ with a confidence interval of 95% [32.37409-43.50091] and demonstrates that $V_\alpha$ is greater for subjects in the experimental group compared to the control group. The analysis demonstrates statistical significance correlating the observed peri-papillary ischemia for those in the experimental group with increased $V_\alpha$ as measured through OCT-A.

TABLE 5

Results of two-tailed test for two dependent means.

| | Experimental Group | Control Group | Analysis |
|---|---|---|---|
| Mean | 49.59375 | 11.65625 | 37.93750 |
| T-test value | | | 13.8046 |
| Standard deviation | 10.361 | 6.168 | |
| SEM | 2.37702 | 1.37924 | |
| df | | | 38 |
| Confidence interval | | | 95% [32.37409-43.50091] |
| p-Value | | | <0.001 |

These models highlighted that the use of retinal photography along with OCT-A could be used to differentiate diagnoses of tick-borne disease to help with early diagnosis or misdiagnosis.

CONCLUSION

Peri-papillary ischemia is a common age-related characteristic demonstrating a white ring surrounding the optic nerve as can be observed by ophthalmoscopy and/or a retinal (fundus) photograph (Miller N R, Arnold A C. Current concepts in the diagnosis, pathogenesis and management of nonarteritic anterior ischaemic optic neuropathy. Eye (Lond). 2015 January; 29(1): 65-79). Ischemic optic neuropathy is the most common optic neuropathy in subjects over age 50. Glaucoma can cause optic neuropathy producing peri-papillary ischemia (Rader J, Feuer W J, Anderson D R. Peripapillary vasoconstriction in the glaucomas and the anterior ischemic optic neuropathies. Am J Ophthalmol 1994 January; 15; 117(1):72-80). However, while glaucoma can occur in subjects younger than 50 years of age, it is predominantly associated with elevated ocular pressure (Park J H, Yoo Y k. Peripapillary Vessel Density in Young Patients with Open-Angle Glaucoma: Comparison between High-Tension and Normal-Tension Glaucoma. J Glaucoma. 2018 November; 27(11):1009-1016; Caprioli, J. & Spaeth, G. L. Comparison of the optic nerve head in high- and low-tension glaucoma. Arch Ophthalmol. 103, 145-1149 (1985)).

Since the subjects were screened for possible increased IOP or asymmetry of the optic nerve and were found negative, the results of the study demonstrate that there is statistical significance of reduction in vessel density within the peri-papillary vessel plexus. This correlates with the measured peri-papillary ischemia of subjects in the experimental group compared to the control group (see Table 5).

Ruling out peri-papillary ischemia will potentially provide a means for early detection of Lyme related infection, and eliminate the risk of the Lyme related infection becoming chronic if not diagnosed for those subjects presenting with visual symptoms. It is proposed that the reason for the peri-papillary ischemia is that a biofilm produced by spirochetes, ranging up to 50 μm in diameter, blocks the blood flow in the narrow peri-papillary plexus of vessels (15 μm in diameter) surrounding the optic nerve. The result is the appearance of a white "halo" completely or partially surrounding the optic nerve.

Equation 1 demonstrates vessel atrophy is matched with the peripapillary ischemia shown in fundus photos. Therefore, the statistical significance of a positive vessel atrophy serves as a biomarker of potential Lyme related infections. Subjects presenting with sudden onset of symptoms in conjunction with the characteristic peri-papillary ischemia are suspects for undiagnosed tick-borne, Lyme related infection. Early detection by optometrists and ophthalmologists should be to screen for the potential of tick-borne infection. Testing should include careful evaluation of the optic nerve peri-papillary area through use of fundus photographs, direct and indirect ophthalmoscopy, and/or OCT-A to rule out peri-papillary ischemia. Primary care physicians will also benefit from performing direct ophthalmoscopy for subjects having visual complaints to screen for the characteristic of peri-papillary ischemia.

The conclusion from this study is that peri-papillary ischemia surrounding the optic nerve is caused by vessel atrophy and is a biomarker of Lyme related infection. The condition of peri-papillary ischemia is easily observed by a fundus photograph or ophthalmoscopy as well as further assessed by OCT-A. Peri-papillary ischemia should be used as a screening for health care professionals for subjects who are symptomatic. This will fortify decision making to rule out Lyme related infection and to establish the retina as a source for further study related to Lyme related infection.

Further Definitions

The above aspects of the present disclosure are meant to be illustrative. They were chosen to explain the principles and application of the disclosure and are not intended to be exhaustive or to limit the disclosure. Many modifications and variations of the disclosed aspects may be apparent to those of skill in the art. Persons having ordinary skill in the art should recognize that components and process steps described herein may be interchangeable with other components or steps, or combinations of components or steps, and still achieve the benefits and advantages of the present disclosure. Moreover, it should be apparent, to one skilled in the art, that the disclosure may be practiced without some or all of the specific details and steps disclosed herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements, and/or steps are in any way required for one or more embodiments. The terms "comprising," "including," "having," and the like are synonymous and are used inclusively, in an open-ended fashion, and do not exclude additional elements, features, acts, operations, and so forth.

Disjunctive language such as the phrase "at least one of X, Y, Z," unless specifically stated otherwise, is understood with the context as used in general to present that an item, term, etc., may be either X, Y, or Z, or any combination thereof, e.g., X, Y, and/or Z. Thus, such disjunctive language is not generally intended to, and should not, imply that certain embodiments require at least one of X, at least one of Y, or at least one of Z to each be present.

As used in this disclosure, the term "a" or "one" may include one or more items unless specifically stated otherwise. Further, the phrase "based on" is intended to mean "based at least in part on" unless specifically stated otherwise.

What is claimed is:

1. A method for identifying an indication for testing for a Lyme-related infection, the method comprising the steps of:
- with respect to a human subject below the age of about 50 years old presenting a sudden onset of at least one visual symptom associated with a Lyme-related infection, screening the subject for peri-papillary ischemia; and
- if peri-papillary ischemia is present, further testing the subject for the Lyme-related infection;
- wherein the further testing comprises testing the subject for one or more of an *Anaplasma* infection, a *Babesia* infection, a *Bartonella* infection, *Borrelia* infection, a *Coxiella* infection, an *Ehrlichia* infection, a Flavivirus infection, a *Francisella* infection, a *Mycoplasma* infection, a Reoviridae infection, and a *Rickettsia* infection.

2. The method of claim 1, wherein the at least one visual symptom is at least one visual symptom selected from the group consisting of photophobia, visual fatigue, eye strain, loss of place, seeing print move on a page when reading, double vision, and headaches.

3. The method of claim 1, wherein screening the subject for peri-papillary ischemia comprises performing at least one optical observation of an optic nerve of the subject.

4. The method of claim 3, wherein performing the at least one optical observation comprises performing at least one of fundus photography, direct ophthalmoscopy, and indirect ophthalmoscopy.

5. The method of claim 1, wherein screening the subject for peri-papillary ischemia comprises performing ocular coherence tomography with angiography (OCT-A).

6. The method of claim 5, wherein screening the subject for peri-papillary ischemia comprises:
- partitioning an image of a peri-papillary area of the subject into quadrants;
- determining a vessel density for each quadrant;
- determining a total vessel density by calculating a sum of the vessel densities of the quadrants;
- determining a normalized vessel density for a healthy eye with no vessel atrophy; and
- determining a vessel atrophy of the peri-papillary area of the subject based on the total vessel density and the normalized vessel density.

7. The method of claim 6, further comprising determining the subject has peri-papillary ischemia when the vessel atrophy is at least about 30%.

8. The method of claim 1, wherein the subject is between the age of about 1 year old and about 50 years old.

9. The method of claim 1, wherein the further testing comprises testing the subject for one or more of an *Anaplasma phagocytophilum* infection, a *Babesia duncani* infection, a *Babesia microti* infection, a *Bartonella henselae* infection, a *Bartonella quintana* infection, a *Borrelia burgdorferi* infection, a *Borrelia hermsii* infection, a *Borrelia lonestari* infection, a *Borrelia parkeri* infection, a *Borrelia turicata* infection, a *Coxiella burnetii* infection, an *Ehrlichia chaffeensis* infection, an *Ehrlichia ewingii* infection, an *Ehrlichia muris* eauclairensis infection, a *Francisella tularensis* infection, and a *Rickettsia rickettsia* infection.

10. The method of claim 1, further comprising, if the subject has the Lyme-related infection, treating the Lyme-related infection of the subject.

11. A method for identifying an indication for testing for a Lyme-related infection, the method comprising the steps of:
- with respect to a human subject below the age of about 50 years old presenting a sudden onset of at least one visual symptom associated with a Lyme-related infection, screening the subject for peri-papillary ischemia using ocular coherence tomography angiography (OCT-A); and
- if peri-papillary ischemia is present, further testing the subject for the Lyme-related infection;
- wherein the further testing comprises testing the subject for one or more of an *Anaplasma* infection, a *Babesia* infection, a *Bartonella* infection, *Borrelia* infection, a *Coxiella* infection, an *Ehrlichia* infection, a *Flavivirus* infection, a *Francisella* infection, a *Mycoplasma* infection, a Reoviridae infection, and a *Rickettsia* infection.

12. The method of claim 11, wherein the at least one visual symptom is at least one visual symptom selected from the group consisting of photophobia, visual fatigue, eye strain, loss of place, seeing print move on a page when reading, double vision, and headaches.

13. The method of claim 11, wherein screening the subject for peri-papillary ischemia comprises:
- partitioning an image of a peri-papillary area of the subject into quadrants;
- determining a vessel density for each quadrant;
- determining a total vessel density by calculating a sum of the vessel densities of the quadrants;
- determining a normalized vessel density for a healthy eye with no vessel atrophy; and determining a vessel atrophy of the peri-papillary area of the subject based on the total vessel density and the normalized vessel density.

14. The method of claim 13, further comprising determining the subject has peri-papillary ischemia when the vessel atrophy is at least about 30%.

15. The method of claim 11, wherein the subject is between the age of about 1 year old and about 50 years old.

16. The method of claim 11, wherein the further testing comprises testing the subject for one or more of an *Anaplasma phagocytophilum* infection, a *Babesia duncani* infection, a *Babesia microti* infection, a *Bartonella henselae* infection, a *Bartonella quintana* infection, a *Borrelia burgdorferi* infection, a *Borrelia hermsii* infection, a *Borrelia lonestari* infection, a *Borrelia parkeri* infection, a *Borrelia turicata* infection, a *Coxiella burnetii* infection, an *Ehrlichia chaffeensis* infection, an *Ehrlichia ewingii* infection, an *Ehrlichia muris* eauclairensis infection, a *Francisella tularensis* infection, and a *Rickettsia rickettsia* infection.

17. The method of claim 11, further comprising, if the subject has the Lyme-related infection, treating the Lyme-related infection of the subject.

* * * * *